US011052122B2

(12) United States Patent
Luquet

(10) Patent No.: US 11,052,122 B2
(45) Date of Patent: *Jul. 6, 2021

(54) LACTIC BACTERIA AND THEIR USE IN THE PREVENTION OF DIARRHEA

(71) Applicant: Kerry Luxembourg S.à.r.l., Luxembourg (LU)

(72) Inventor: Francois-Marie Luquet, Orsay (FR)

(73) Assignee: Kerry Luxembourg S.à.r.l., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 16/155,502

(22) Filed: Oct. 9, 2018

(65) Prior Publication Data

US 2019/0038683 A1    Feb. 7, 2019

Related U.S. Application Data

(60) Division of application No. 15/597,613, filed on May 17, 2017, now Pat. No. 10,124,026, which is a continuation of application No. 13/109,287, filed on May 17, 2011, now abandoned, which is a division of application No. 11/570,752, filed as application No. PCT/CA2005/000954 on Jun. 20, 2005, now abandoned.

(30) Foreign Application Priority Data

Jun. 18, 2004 (CA) .................. CA 2470090

(51) Int. Cl.
*A61K 35/747* (2015.01)
*A23L 33/135* (2016.01)
*A61K 35/00* (2006.01)

(52) U.S. Cl.
CPC .......... *A61K 35/747* (2013.01); *A23L 33/135* (2016.08); *A23V 2002/00* (2013.01); *A23Y 2220/17* (2013.01); *A61K 2035/11* (2013.01)

(58) Field of Classification Search
CPC .......... C12R 1/23; C12R 1/245; A61K 35/747
See application file for complete search history.

(56) References Cited

U.S. PATENT DOCUMENTS

| | | | |
|---|---|---|---|
| 5,902,578 A | 5/1999 | Halpin-Dohnalek et al. | |
| 6,607,905 B1 | 8/2003 | Luquet | |
| 10,124,026 B2* | 11/2018 | Luquet | A23L 33/135 |
| 2012/0107289 A1 | 5/2012 | Luquet | |
| 2017/0266242 A1 | 9/2017 | Luquet | |

FOREIGN PATENT DOCUMENTS

| WO | WO9735596 | 10/1997 |
|---|---|---|
| WO | WO9823727 | 6/1998 |
| WO | WO9959413 | 11/1999 |
| WO | WO0054788 | 9/2000 |
| WO | WO2004037191 | 5/2004 |

OTHER PUBLICATIONS

Bartlett, "Antibiotic-Associated Diarrhea," New England Journal of Medicine, Jan. 31, 2002, 346(5): 334-339. 6 pages.
Beaugerie et al., "Antibiotic-associated diarrhoea," Best Practice & Research Clinical Gastroenterology, 2004, 18(2): 337-352. 16 pages.
Calcium Carbonate (OTC), Medscape, Retrieved Jun. 7, 2017, at http://reference.medscape.com/drug/tums-calcium-carbonate-341983#5, 1 page.
Calcium Carbonate: Human health effects, National Library of Medicine HSDB Database, Retrieved Jun. 7, 2017, at https://toxnet.nlm.nih.gov/cgi-bin/sis/search/a?dbs+hsdb:@term+©DOCNO+927, 70 pages.
Calcium Carbonate Chewable Tablet: Highlights for Calcium-Carbonate , Healthline, Retrieved Jun. 7, 2017, at http://www.healthline.com/drugs/calcium-carbonate/chewable-tablet#Highlights1, 4 pages.
Calcium Carbonate Tablet, WebMD, retrieved Jun. 7, 2017, at http://www.webmd.com/drugs/2/drug-579-2123/calcium-carbonate-oral/calcium-carbonate-antacid-oral/details, 3 pages.
Cheng et al., "Effect of fermented soy milk on the intestinal bacterial ecosystem," Feb. 28, 2005, World Journal of Gastroenterology: WJG. vol. 11, No. 8, pp. 1225-1227. 3 pages.
Chicoine et al., "Emploi des ferments lactiques dans la gastroenterite non bacterienne," L'Union Medicale du Canada, 1973m pp. 1114-1115, vo. 102 (English language summary included).
Clements et al., "Lactobaccillus prophylaxis for diarhea due to enterotoxigeneic *Escherichia coli*," Antimicrobial Agents and Chemotherapy, 1981, pp. 104-108, vol. 20, No. 1.
Conway, et al., "Does eating yogurt prevent antibiotic-associated diarrhea? A placebo-controlled randomised controlled trial in general practice", British Journal of General Practice, Dec. 2007, vol. 57, pp. 953-959.
Cremonini et al., "Effect of Different Probiotic Preparations on Anti-Helicobacter pylori Therapy-Related Side Effects: A Parallel Group, Triple Blind, Placebo-Controlled Study," American Journal of Gastroenterology, Nov. 2002, 97(11): 2744-2749. 6 pages.
D'Souza et al., "Probiotics in prevention of antibiotic associated diarrhea," BMJ, 2002, pahes 1-6, vol. 324.
De Dios Polo-Olano et al., "Effect of a lactobacilli preparation on traveler's diarrhea: A randomized, double blind clinical trial," Gastroenterology, 1978, pp. 829-830, vol. 74, No. 5.
Dendukuri et al., "Probiotic therapy for the prevention and treatment of Clostridium difficile-associated diarrhea: a systematic review," CMAJ, Jul. 19, 2005, vol. 173, No. 2, pp. 167-170.
Food and Agriculture Organization of the United Nations and the World Health Organization, "Joint FAO/WHO Working Group Report on Drafting Guidelines for teh Evaluation of Probiotics in Food," 2002, pp. 1-11.

(Continued)

*Primary Examiner* — Ruth A Davis
(74) *Attorney, Agent, or Firm* — Sughrue Mion, PLLC

(57) ABSTRACT

The present invention concerns a lactic composition useful for the prevention or treatment of diarrhea such as antibiotic associated diarrhea or "tourista." The composition according to the invention contains at least a bacterial strain selected from the group consisting of *Lactobacillus acidophilus*, *Lactobacillus acidophilus* I-1492, *Lactobacillus casei* and a mixture of thereof.

23 Claims, 4 Drawing Sheets

(56) References Cited

OTHER PUBLICATIONS

Gao et al., "Dose-Response Efficacy of a Proprietary Probiotic Formula of Lactobacillus acidophilus CL1285 and Lactobacillus casei LBC80R for Antibiotic-Associated Diarrhea and Clostridium difficile-Associated Diarrhea Prophylaxis in Adult Patients," American Journal of Gastroenterology, Feb. 9, 2010, 105(7): 1636-1641. 6 pages.
Greger et al., "Aluminum exposure and metabolism" 1997, Critical Reviews in Clinical Laboratory Sciences, vol. 34, No. 5, pp. 439-474, 37 pages.
Greger, J., "Aluminum Metabolism", Jul. 1993, Annula Review of Nutrition, vol. 13, No. 1, pp. 46-63, 21 pages.
Guerin et al., "Protection of bifidobacteria encapsulated in polysaccharide-protein gel beads against gastric juice and bile," Nov. 2003, Journal of Food Protection. vol. 66, No. 11, pp. 2076-2084. 9 pages.
Health Canada requests information from industry on the use of aluminum-containing food additives. Health Canada—Food and Nutrition. Retrieved Jun. 7, 2017, Published Jun. 24, 2013 at http://www.hc-sc.gc.ca/fn-an/securit/addit/aluminum_stake-eng. php, 3 pages.
Health Canada Review of dietary exposure to aluminum: Background. Health Canada: Food and Nutrition. Retrieved Jun. 7, 2017, Published on Jun. 24, 2013, at http://www.hc-sc.gc.ca/fn-an/securit/addit/aluminum-eng.php, 4 pages.
Herzog et al., "Antacid therapy—Changes in mineral metabolism," Dec. 1981, Scandinavian journal of gastroenterology. Supplement. vol. 75, pp. 56-62, 7 pages.
Heyman, "Effect of lactic acid bacteria on diarrheal diseases," Journal of the American College of Nutrition, 2000, vol. 19, No. 2, pp. 137S-146S.
Insogna et al., "Osteomalacia and weakness from excessive antacid ingestion," Dec. 5, 1980, JAMA. vol. 244, No. 22, pp. 2544-2546. 3 pages.
Kailasapathy, K., "Microencapsulation of probiotic bacteria: Technology and potential applications," Sep. 2002, Current issues in intestinal microbiology, vol. 3, No. 2, pp. 39-48, 11 pages.
Kirschbaum et al., "Acute aluminum toxicity associated with oral citrate and aluminum-containing antacids," Jan. 1, 1989, The American journal of the medical sciences. vol. 297, No. 1, pp. 9-11, 3 pages.
Krewski et al., "Human health risk assessment for aluminum, aluminum oxide, and aluminum hydroxide," Nov. 16, 2007, Journal of Toxicology and Environmental Health, Part B. vol. 10 (Supplemental 1), 337 pages.
Marteau et al, "Protection from gastrointestinal diseases with the use of probiotics 1-3," Am. J. Clin. Nutr., 2001, pp. 430S-436S, vol. 73.
Millette et al., "Gastrointestinal survival of bacteria in commercial probiotic products," Nov. 1, 2013, International Journal of Probiotics & Prebiotics. vol. 8, No. 4, 8 pages.
Pearce et al., "Controlled trial of orally administered lactobacilli in acute infantile diarrhea," Journal of Pediatrics, 1974, pp. 261-262, vol. 84, No. 2.
Plummer, et al. "Estudio piloto de Clostridium difficile: efecto del aporte suplementario de probioticos sobre la incidencia de diarrea causada por C. difficile.," International Microbiology 2004, vol. 7, No. 1, pp. 59-62.
"Probiotics in Food: Health and Nutritional Properties and Guidelines for Evaluation," FAO Food and Nutrition Paper 85: Report of a Joint FAO/WHO Working Group on Drafting Guidelines for the Evaluation of Probiotics in Food. Ontario, Canada, Apr. 30-May 1, 2002, pp. 36-56, 56 pages.
Psaradellis et al., "Efficacy of BIO K+ CL1285(R) in the reduction of antibiotic-associated diarrhea—a placebo controlled double-blind randomized, multi-center study," Arch Med Sci, 2010, vol. 6, No. 1, pp. 56-64.
Reid et al., "Microentrapment of probiotic bacteria in a Ca2+-induced whey protein gel and effects on their viability in a dynamic gastro-intestinal model," 2005, Journal of Microencapsulation. vol. 22, No. 6, pp. 603-619. 17 pages.
Reid, et al. "Potential uses of probiotics in clinical practice," Clinical microbiology reviews, 2003, vol. 16, No. 4, pp. 658-672.
Rossi et al., "Effect of a new fermented soy milk product on serum lipid levels in normocholesterolemic adult men," Mar. 2003, Archivos latinoamericanos de nutricion. vol. 53, No. 1, pp. 47-51. 8 pages.
Rossi et al., "Effects of a novel fermented soy product on the serum lipids of hypercholesterolemic rabbits," Mar. 2000, Arquivos brasileiros de cardiologia, vol. 74, No. 3, pp. 213-216. 4 pages.
Rowland et al, "Current Level of Consensus on Probiotic Science—Report of an expert meeting," London, Great Britain, Nov. 23, 2009, 8 pages.
Sodium aluminosilicate, Food and Drug Adminstration CFR 21 Sec 182.2727. Published Sep. 21, 2016, at https://www.accessdata.fda.gov/scripts/cdrh/cfdocs/cfcfr/CFRSearch.cfm?fr=182.2727, 2 pages.
Spencer et al., "Adverse effects of aluminum-contained antacids on mineral metabolism," Mar. 1979, vol. 76, No. 3, pp. 603-606, 5 pages.
Supplementary European Search Report dated Aug. 5, 2009 for European Application No. EP05757612.
Tankanow et al, "A double-blind, placebo-controlled study of the efficacy of Lactinex in the prophylaxis of amoxicillin-induced diarrhea," DCIP, The Annals of Pharmacotherapy, 1990, pp. 382-384, vol. 24.
Thomas et al., "Lack of Effect of Lactobacillus GG on antibiotic-Associated Diarrhea: A Randomized, Placebo-Controlled Trial," Mayo Clin Proc., 2001, vol. 76, pp. 883-889.
Vanderhoof et al., "Use of Probiotics in Childhood Gastrointestinal Disorders," Journal of Pediatric Gastroenterology & Nutrition, 1998, pp. 1-33, vol. 27, No. 3.
Wolvers et al., "Guidance for Substantiating the Evidence for Beneficial Effects of Probiotics: Prevention and Management of Infections by Probiotics1-3," The Journal of Nutrition, Jan. 27, 2010, vol. 140, pp. 698S-712S.
Xu et al., "Conjugated linoleic acid content and organoleptic attributes of fermented milk products produced with probiotic bacteria," Nov. 2005, Journal of Agricultural and Food Chemistry, vol. 53, No. 23, pp. 9064-9072, 9 pages.

\* cited by examiner

Figure 1 : Patient distribution

\* : initially, ≥ 24hours
§: NPO : *nil per os*; TNP : total parenteral nutrition Figure 2: DAA incidence according to category of received antibiotic Figure 3: Results of the study described in Example 1

LACTIC BACTERIA AND THEIR USE IN THE PREVENTION OF DIARRHEA

CROSS REFERENCE TO RELATED APPLICATIONS

The present application is a divisional of U.S. Ser. No. 15/597,613 filed May 17, 2017, which is a continuation of U.S. Ser. No. 13/109,287, filed on May 17, 2011, now abandoned, which is a divisional of U.S. Ser. No. 11/570,752, filed on Jun. 28, 2007, now abandoned, which is a national stage filing under 35 U.S.C. § 371 of international application No. PCT/CA2005/000954, filed on Jun. 20, 2005, which claims the benefit of Canadian application No. 2,470,090, filed on Jun. 18, 2004. The entire contents of each of these priority applications are incorporated herein by reference.

FIELD OF THE INVENTION

The present invention relates to the use of lactic bacteria strains in the prevention of diarrhea. More particularly, the present invention concerns the use of lactic bacteria in order to prevent antibiotic associated diarrhea (AAD).

DESCRIPTION OF PRIOR ART

Diarrhea may be caused by a temporary problem, like an infection, or a chronic problem, like an intestinal disease. A few of the more common causes of diarrhea are listed below:

Bacterial infections: Several types of bacteria, consumed through contaminated food or water, can cause diarrhea such as *Campylobacter, Salmonella, Shigella,* and *Escherichia coli.*

Viral infections: Many viruses cause diarrhea, including rotavirus, Norwalk virus, cytomegalovirus, herpes simplex virus, and viral hepatitis.

Parasites. Parasites can enter the body through food or water and settle in the digestive system. Parasites that cause diarrhea include *Giardia lamblia, Entamoeba histolytica,* and *Cryptosporidium.*

Reaction to medication, such as antibiotics, blood pressure medications, and antacids containing magnesium.

Intestinal diseases like inflammatory bowel disease or celiac disease.

Functional bowel disorders, such as irritable bowel syndrome, in which the intestines do not work normally.

About 10% of all antibiotic treatments are known to be responsible for gastrointestinal side-effects, notably diarrhea called antibiotic associated diarrhea (AAD).

All groups of antibiotics may cause AAD, but those with broad-spectrum coverage, such as cephalosporins, extended-coverage penicillins, and clindamycin, are the most common causes of AAD.

The incidence of AAD, from 5 to 39%, has been on the rise in the past years, particularly following the increased utilisation of wide spectrum antibiotics (Bergogne-Berezin, 2000; McFarland, 1998; Spencer 1998). The clinical presentation of AAD is very variable, ranging from an uncomplicated diarrhea to a pseudomembranous colitis.

It should be noted that 10 to 20% of cases of AAD are caused by a *Clostridium difficile* (*C. difficile*) infection (Bergogne-Berezin, 2000; Bartlett, 2002). *C. difficile* is an anaerobic gram-positive rod. *C. difficile* diarrhea is largely a nosocomial disease and it is the most frequent cause of diarrhea in hospitalized patients. Its occurrence in the outpatient setting, other than in patients confined to nursing homes, is much less common.

*C. difficile* diarrhea is used to describe a wide spectrum of diarrheal illnesses caused by the potent toxins produced by this organism, including cases of severe colitis with or without the presence of pseudomembranes.

In particular this organism can be isolated in a great number of AAD cases with evidence of colitis and in all those with pseudomembranes. It is widely present in the environment and may survive for a considerable time. It is transmitted by the fecal-oral route to susceptible individuals. It is considered part of the normal flora of infants and can be isolated in about 5% of healthy adults and in up to one third of asymptomatic or colonized, hospitalized patients.

Both *C. difficile* toxins A and B exhibit potent enterotoxin and cytotoxic effects that are responsible for the clinical manifestations.

AAD, and more particularly *C. difficile* AAD, may subsequently bring about important consequences at the financial level as well as at the clinical level: increase of the morbidity, of the mortality, of the number of hospitalisations as well as the duration of these (McFarland, 2002). It is observed that the development of a *C. difficile* AAD presents a risk not only for the patient undergoing antibiotic therapy, but also for the other patients hospitalized in the same care unit, given the contagious character of this diarrhea (Bartlett, 2002).

Epidemiologic studies have shown that *C. difficile* is often isolated in hospital wards, including the floors, door handles, and furniture even weeks after patients with AAD have been removed from the area. Less frequently, similar observations have been made among asymptomatic medical personnel and in hospital wards occupied by unaffected patients. Patients readmitted after recent hospitalizations are found to have a high prevalence of *C. difficile* colonization, which represents an important source of infection. Because of the sporulating properties of this organism, all these observations suggest an important role for cross-contamination between patients, contact with environmental surfaces, and transmission via hands of medical personnel.

Many antimicrobials have been used to treat *C. difficile* colitis. The development of effective preventive measures against AAD thus seems unavoidable.

Lactic Acid Bacteria

It is the scientist E. Metchnikoff (1845-1919) who proposed that the longevity and the health of the Bulgarian people is attributable to their ingestion of fermented milk products. It was well known that certain bacteria are pathogenic to the organism. Thus, it was proposed that these bacteria be substituted by yogourt bacteria since the latter had long been used without fear. Many standard guidelines have been established in order to define a good lactic acid bacterium. Among these standards are: they must conserve their activity and their viability prior to consumption, they must survive the gastrointestinal tract, they must be able to survive and to proliferate in the intestines, and must eventually produce beneficial effects. In addition, the microorganisms must not be pathological nor toxic.

Many trials have been conducted in order to improve the state of health by modifying the intestinal flora through living lactic acid bacteria. Today, the beneficial effects of these lactic acid bacteria are well identified and there are attempts to explain the mechanism(s) related to such benefits. Salminen's team has summarized the most important beneficial effects, supported by scientific evidence such as immunological modulation and reinforcement of the intestinal mucous barrier. Different mechanisms are proposed in order to explain to what such benefits would be due: the modification of the intestinal flora, adherence to the intestinal mucous membrane with the capacity of preventing the adherence of pathogenic bacteria or the activation of pathogens, the modification of food proteins by intestinal microflora, the modification of bacterial enzymatic capacity, and finally the influence on the permeability of intestinal mucosa.

Many studies indicate a therapeutic potential of lactic acid bacteria and yogurt which is mainly due to the change in grastro-intestinal micro-ecology. The efficiency of lactic acid bacteria is enhanced by their capacity of adherence to the intestinal wall since the adherent bacterial strains have a competitive advantage, important to maintain their place in the gastro-intestinal tract. On the other hand, no bacterial strain has yet been shown to adhere in a permanent fashion. By increasing the quantity of lactic acid bacteria in the intestines, it is possible to eliminate growth of pathogenic bacteria, which in turn will contribute to a reduction of infections. An intact intestinal epithelium with an optimal intestinal flora represents a barrier against invasions or colonisation by pathogenic micro-organisms, antigens and harmful compounds for the intestinal tract.

In general, the consumption of lactic acid bacteria acts by a reinforcement of the non-specific immune response or acts as an adjuvant in the antigen-specific immune response. Studies on animals have demonstrated that the lymphoid tissue associated to the intestines is stimulated by living lactic acid bacteria, resulting in a production of cytokines and antibodies (IgA) and an increase of mitogenic activity of the cells forming Peyer plaques and splenocytes. In the studies on human cells, the production of cytokine, phagocytic activity, antibody production, the function of T cells and NK cell activity are increased by the consumption of yogurt or when the cells are exposed to lactic acid bacteria in vitro.

Evidence exists that the yogurt stimulation of the immune system may be associated with the reduction of pathological incidences like cancer, gastro-intestinal disorders and allergy symptoms.

Lactic acid bacteria are also known as probiotics. The term "probiotic" describes dietary supplements composed of living micro-organisms destined to enhance health (D'Souza et al., 2002). The most frequently used species are *Lactobacillus* spp., *Bifidobaterium* spp. and *Saccharomyces* spp. (Cremonini et al., 2002; Lu et al., 2001; Lewis et al., 1998; D'Souza et al., 2002; Isolauri, 2001). Many mechanisms of action have been proposed to explain their efficacy, such as the production of antimicrobial substances, the competition for gastro-intestinal colonisation as well as for available nutrients, immunomodulation and the promotion of lactose digestion (Lu et al., 2001; D'Souza et al., 2002; Alvarez-Olmos et al., 2001).

Many studies, both in vitro and in vivo, have demonstrated that Lactobacilli (in particular, *L. acidophilus*) are not just normal inhabitants of the intestinal tract. Lactobacilli also play an important role in stimulating the immune system, inhibiting pathogens and lowering colon cancer risks.

Moreover, the effects of probiotics on general health are numerous. Probiotics are known to enhance intestinal health, improve digestion, strengthen the immune system, reduce blood cholesterol and reduce the HDL/LDL ratio. Probiotics have also been tried in AAD.

Several researchers have concluded that probiotics are effective in the treatment of acute infectious diarrhea in children and in the prevention of AAD and nosocomial/community acquired diarrhea (Gill and Garner, 2004). In a meta-analysis of over 20 studies, Cornelius et al. (2004) suggested that *Lactobacillus* is a safe and effective treatment of acute diarrhea in children. Moreover, it has been shown that a child-care formula supplemented with *Lactobacillus reuteri* or *Bifidobacterium lactis* reduced the episodes and duration of diarrhea in infants (Weizman et al. 2005). U.S. Pat. No. §,887,465 to Reniero et al., discloses the use of *Lactobacillus* strains for preventing diarrhea caused by pathogenic bacteria and rotaviruses in children from 35 to 70 months old.

Probiotics are thought to be potentially efficient to limit the proliferation of secondary pathogens when antibiotics are taken. However, to this day the medical profession remains prudent as to the use of probiotics in common practice, partly because few studies with solid specifications supporting their efficiency in primary prevention of AAD have been published (Lewis et al., 1998). In one of these studies, Plummer et al. (2004) reported a reduction of incidence in the *C. difficile* associated toxins in the group of elderly patients under study that had received a probiotic capsule containing $2 \times 10^{10}$ cfu of *Lactobacillus acidophilus* and *Bifidobacterium bifidum*.

However, Pereg et al. (2005) also observed a nonsignificant trend for reduction of the incidence of diarrhea among healthy young adults consuming yogourt containing *Lactobacillus casei*. Thus, the efficacy of probiotics in the prevention of AAD in adults shows conflicting results and needs to be further evaluated in adults. (Szajewska and Mrukowicz, 2005).

The majority of published studies use lyophilized probiotics in the form of a capsule and different strains are evaluated. However, it is important to mention that all probiotics do not act in the same manner and that they may have different clinical efficiencies. The results obtained in the different studies should therefore not be considered valid for strains other than those evaluated in these trials (Cremonini et al., 2002; D'Souza et al., 2002).

There is thus a need for new compositions in order to improve the prevention or cure of diarrhea and especially diarrhea associated to curative antibiotic therapy prescribed to patients.

SUMMARY OF THE INVENTION

An object of the present invention is to provide a product that satisfies the above-mentioned need.

The present invention thus relates to a composition for prevention or treatment of diarrhea in a mammal, characterized in that it comprises an effective amount of at least a lactic bacterium strain and a pharmaceutically acceptable vehicle.

The present invention also relates to the use of the composition of the invention for the prevention or treatment of diarrhea in a mammal.

The present invention further relates to the use of at least a lactic bacterium strain for the manufacture of a composition destined to the prevention or treatment of diarrhea in a mammal.

The present invention relates as well to the method of prevention or treatment of diarrhea, characterized in that it comprises the step of administering to a mammal an effective amount of the lactic composition according to the invention.

Moreover, the present invention relates to a kit for prevention or treatment of diarrhea, characterized in that it comprises at least a container containing the composition of the invention.

An advantage provided by the method of the present invention is that it greatly reduces or eliminates the risk of occurrence of AAD and also eliminates the risk of cross-contamination in hospitals and thereby reduces or eliminates the risk of death caused by AAD.

Another advantage of the present invention is that it provides a non toxic prevention or treatment of AAD.

A third advantage of the present invention is that it provides a non-invasive method of prevention or treatment of AAD.

Another advantage of the present invention is that it provides a method of prevention or treatment of AAD that does not require the use of antibiotics. This will prevent the occurrence of side effects caused by the incompatibility between drugs.

Another advantage of the present invention is also that it provides a composition that can be used over a prolonged period of time for prevention or treatment of AAD, which presents little or no side effects. Such composition is readily available in health food stores or specialized markets without the need for a prescription.

Another advantage of the present invention is that it provides a composition, which reaches the guts mucosa in a proper and viable form without getting destroyed in the upper part of the gastrointestinal tract, especially in the stomach. Another advantage of the present invention is that it also provides a composition, which contains a sufficient number of bacteria capable of getting implanted in the guts.

Another advantage of the present invention is that it provides a composition to be administered to adults and children alike. This composition can be administered in a hospital milieu, at home, in child-care facility or any facility where prevention and control of diarrhea is needed.

Another advantage of the present invention is that it provides a composition easily administered as a food or food supplement.

Other objects and advantages of the present invention will be apparent upon reading the following non-restrictive detailed description, made with reference to the accompanying drawings

BRIEF DESCRIPTION OF THE TABLES

Figure 1:
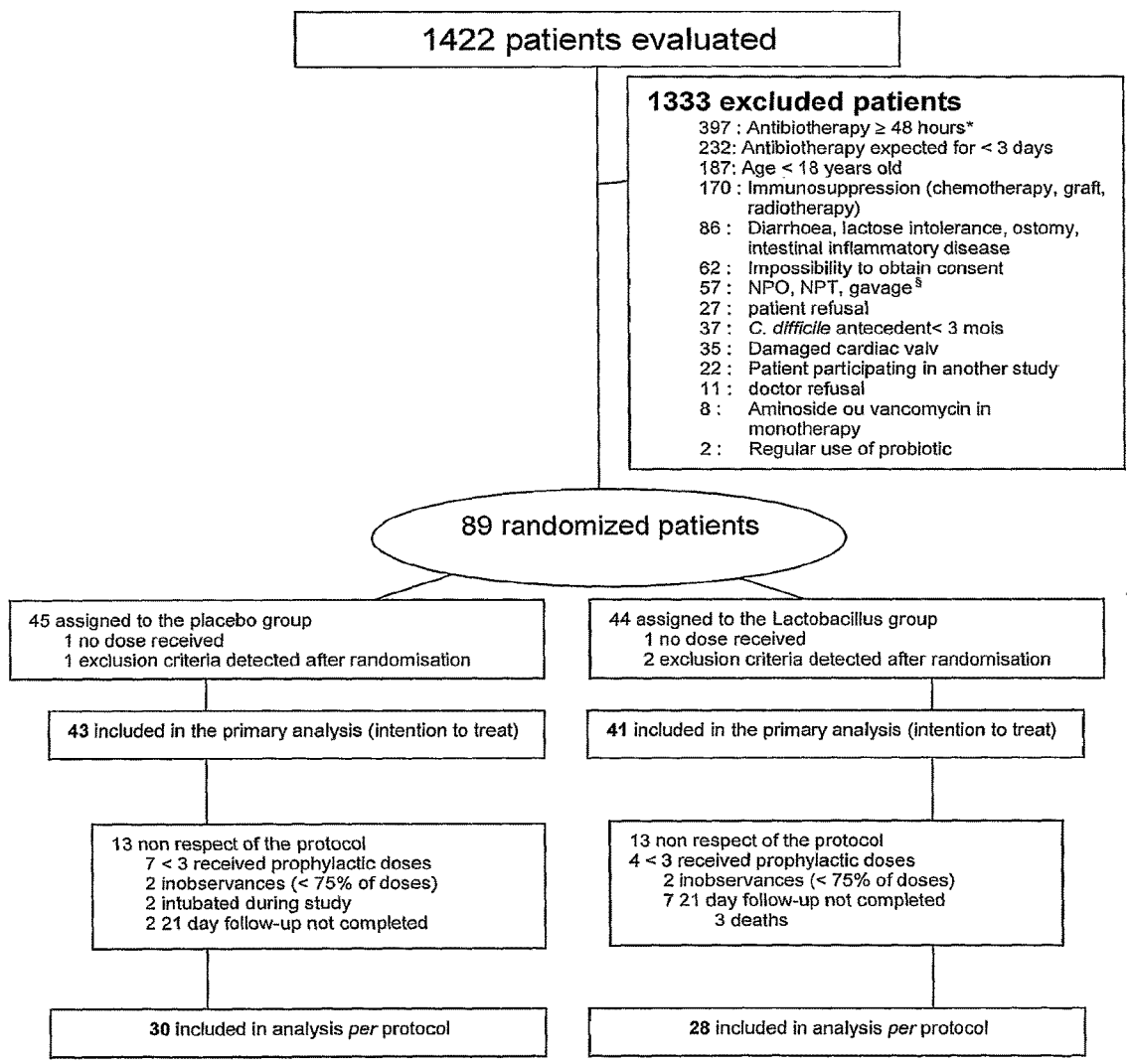
FIG. 1 is a schematic illustration of the distribution of patients for the study described in Example 1.

Table I shows the basic characteristics of 89 randomized patients of Example 1

Table II shows the incidence and severity of AAD and hospitalisation duration in Example 1.

Table III shows the undesirable effects reported during the study on Example 1.

DETAILED DESCRIPTION OF THE INVENTION

In order to provide an even clearer and more consistent understanding of the description, including the scope given herein to such terms, the following definitions are provided:

By "mammal", we mean any living organism, which can be subjected to AAD, and this includes vertebrate such as in particular notably, human beings, domestic and wild animals.

By "diarrhea" it is meant loose, watery stools occurring more than three times in one day.

By "antibiotic associated diarrhea AAD" it is meant diarrhea due to antibiotic treatment.

By "prevent, prevention", we mean a process by which AAD is eradicated or slowed.

By "treat", it is meant a process by which the symptoms of AAD are maintained at a constant level, reduced or completely eliminated. As used herein, "treatment" means any manner in which the symptoms of conditions, disorder or disease are ameliorated or otherwise beneficially altered. Treatment also encompasses any pharmaceutical use of the compositions herein. "Treatment" also refers to both therapeutic treatment and prophylactic or preventative measures. Those in need of treatment include those already with the disorder as well as those prone to have the disorder or those in which the disorder is to be prevented. As used herein, the term "treating a bacterial infection" refers to a process whereby the metabolic activity of a bacterium or bacterial population in a host, preferably a mammal, more preferably a human, is inhibited or ablated.

By "pharmaceutically acceptable", we mean a vehicle, which may be administered without any risk to a mammal, in particular to a human being, and this with few or no negative or toxic secondary effects. Such a vehicle may be used for different functions. For example, it can be used as a preservation, solubilizing, stabilizing, emulsifying, softening, coloring, odoring, or as an antioxidizing agent. These types of vehicles may be easily prepared by using methods well known to a person skilled in the art.

By "probiotoc", it is meant live microorganisms, including *Lactobacillus* species, *Bifidobacterium* species and yeasts, that may beneficially affect the host upon ingestion by improving the balance of the intestinal microflora.

By "about", it is meant that the value of the number of micro-organisms, the weight of the unit of the composition or the number of days of refrigeration can vary within a certain range depending on the margin of error of the method used to evaluate such number.

By "nutritionally acceptable", it is meant a vehicle that can be administered without risk to a mammal, in particular to a human, and this with little or no negative or toxic side effects. Such a vehicle can be used for different functions. For example, it can be used as a preservation, solubilizing, stabilizing, emulsifying, softening, coloring, odoring agent, or as an antioxidant agent. These types of vehicles may be easily prepared by using methods well known by a person in the art.

The present invention relates to a composition for prevention or treatment of diarrhea in a mammal more preferably antibiotic associated diarrhea, comprising an effective amount of at least a lactic bacterium strain and a pharmaceutically acceptable vehicle. In a preferred embodiment the lactic bacterium strain is selected from the group consisting of: *L. acidophilus, L. casei* and a mixture thereof. In a preferred embodiment, the lactic bacterium strain is of the genus *Lactobacillus*. In yet another preferred embodiment, the *L acidophilus* strain is at least strain I-1492 deposited at the CNCM.

In a preferred embodiment the composition of the invention comprises at least about 0.5 billion of living and active micro-organisms of the *L. acidophilus* strain per gram of the composition, up to about 120 days under refrigeration. In a more preferred embodiment the composition of the invention comprises about 50 billions, of a population of living and active micro-organisms of the *L acidophilus* strain, per unit of the composition, up to about 120 days under refrigeration, where at least about 80% are micro-organisms of the *L. acidophilus* 1-1492 deposited at the CNCM. The composition of the invention may also comprise at least about 100 billions of a population of living and active micro-organisms of the *L. acidophilus* strain, per unit of the composition, up to about 90 days under refrigeration, where at least about 80% are micro-organisms of the *L acidophilus* 1-1492 deposited at the CNCM. By "unit", it is meant any container suitable for commercial use, which contains about 98 grams of the composition of the invention, such as, but not limited to, a jar or a plastic container usually used for containing dairy products such as yogurts, or other ferments.

According to another preferred embodiment of the invention, the composition comprises the Bio-K Plus™ products. According to yet another preferred embodiment of the invention, the lactic composition of the invention further comprises fermented milk proteins and fermented soy proteins. Bio-K Plus™ products are lactic ferment products readily available on the market and sold by the company Bio-K Plus International Inc. The Bio-K Plus™ products contains *Lactobacillus acidophilus* and *Lactobacillus casei*, and more specifically *Lactobacillus acidophilus* 1-1492 CNCM. The composition of the invention contains thus about 95% of *Lactobacillus acidophilus* and about 5% of *Lactobacillus casei*.

As mentioned above, the diarrhea is preferably but not limited to an antibiotic associated diarrhea. About 10% of all antibiotic treatments are known to be responsible for gastrointestinal side-effects, notably antibiotic associated diarrhea (AAD). All groups of antibiotics may cause AAD, but those with broad-spectrum coverage, such as cephalosporins, extended-coverage penicillins, and clindamycin, are the most common causes of AAD. From 10 to 20% of AAD cases are caused by a *Clostridium difficile* (*C. difficile*) infection (Hogenauer et al., 1998; Bartlett, 2002). Hence, in preferred embodiment of the invention, the composition of the invention is for prevention or treatment of diarrhea in a mammal caused by *C. difficile*. However, the composition of the invention may also be used in the prevention or treatment of diarrhea of the type "tourista". In a preferred embodiment, the mammal is a human being.

A person skilled in the art will know how to prepare compositions that are nutritionally acceptable and determine, in function of many factors, the privileged method of administration and the quantity that should be administered. Among the factors that can influence his choices are: the exact nature of the ingredients, active or not, entering in the composition; the condition, the age and the weight of the mammal, the stage of AAD and the nature of the treatment.

According to another aspect, the invention proposes the use of the composition of the invention for the prevention or treatment of diarrhea in a mammal.

According to another aspect, the invention proposes the use of a lactic bacterium strain for the manufacture of the composition of the invention. In a preferred embodiment, the *Lactobacillus acidophilus* strain other than 1-1492; and the *Lactobacillus casei* strain may be of commercial origin and can be purchased from manufacturers of lactic ferments.

For preparing a composition according to the present invention at least one of the *Lactobacillus* strains according to the present invention is incorporated in a suitable support, in an amount of from about 50 billions to about 100 billions micro-organisms per unit of about 98 g of the composition.

The composition according to the present invention can be obtained by fermenting the lactic bacteria in a milk-based medium. For this purpose, the following process may be used.

Firstly, the 1-1492, *Lactobacillus acidophilus* and *casei* strains are incubated in a MRS type fermentation medium under 10% of $CO_2$ according to a standard program comprising several steps. The recombined lacteal base, which is partially lactose-free and degassed, is pasteurized for 1.5 minutes at 95° C. and inoculated at 10%. Finally, it is incubated according to the following program:
1) the 1-1492 strain: 2 hours at 37° C. under 10% $CO_2$;
2) the *acidophilus* strain: 2 hours at 37° C. and
3) the *casei* strain: 1 hour at 37° C.

The product is then co-fermented in an anaerobic atmosphere and medium for 15 hours at 37° C. (degassing under $CO_2$).

In order to realize the invention, any *acidophilus* and *casei* strains may be used as long as they present no health risk. The total concentration of Lactobacilli *acidophilus* (including those obtained from 1-1492 strains) which is present in the composition of the invention, must be at least equal to 50 billion per unit of 98 g of the composition and the concentration of 1-1492 must be at least 80% of the total number of micro-organisms per unit of about 98 g of the composition.

Although total amino acid content is similar to milk, free amino acids are preferably significantly higher. The level of peptides comprised in the composition of the invention, having a molecular weight between 1000 and 5000 Da. is around 30% and the level of small peptides having less than 10 residues is approximately 15%. It is known that such levels of peptides fortify, in a surprising way, the immune and digestive systems.

The quantity or the concentration of lactic bacteria which is administered to a human or an animal, or that is present in the composition of the invention is a therapeutically effective quantity. A therapeutically efficient quantity of lactic bacteria is the necessary quantity to obtain positive results without causing excessively negative effects in the host to which the lactic bacteria or the composition is administered. Indeed, an efficient quantity of lactic bacteria to prevent AAD is a quantity, which is sufficient to attenuate or reduce in any manner the symptoms linked to AAD. An effective amount can be administered in one or more administrations, according to a regimen. For example, as mentioned above, an efficient quantity according to a preferred embodiment of the invention is about 50 to about 100 billions bacteria per unit of about 98 g of the composition. Such a quantity may be administered in a single dose or may be administered by another regime according to which it is efficient. However, it is understood that the exact quantity of lactic bacteria or of each of the components of the composition and the quantity of the composition to be administered will vary according to factors such as the type of AAD to prevent, the other ingredients in the composition, the mode of administration, the age and the weight of the mammal, etc. . . . .

The composition according to the present invention can be presented as a solid or a liquid form, usual for pharmaceutical or nutritional administration, i.e. for example liquid forms of administration, in a gel, capsule or any other support known to the person skilled in the art. Among the usable compositions, we can notably cite the compositions that can be administered orally. In the present case, the composition of the invention can be administered as food form (for example a lactic ferment) or as food supplements. More particularly, the composition according to the present invention can be presented in a variety of ingestable forms, such as e.g. milk, yogurt, curd, fermented milks, milk based fermented products, soy based fermented products, fermented cereal based products, milk based powders and infant formulae. The composition can also be administered in the form of food or food supplements. Such foods may be protein concentrates such as those used in hospitals.

In case of a pharmaceutical preparation the product may be. prepared in forms of but not limited to capsules, tablets, liquid bacterial suspensions, dried oral supplements, wet oral supplements, dry tube feeding or a wet tube feeding etc., with the amount of *Lactobacillus* strains to be incorporated therein being in the range of up to but not limited to 30 billions.

The present invention also concerns a method for prevention or treatment of diarrhea, comprising the step of administering to a mammal an effective amount of the lactic composition of the invention. In preferred embodiment the administration is an oral administration. In a preferred embodiment, the composition is administered at the rate of about 49 g per day for the first two days and then at the rate of about 98 g per days for the next period of at least 10 days.

As a preventive measure and for general maintenance of the intestinal transit and health, it is recommended to preferably take about 98 g per day of the composition of the invention. As general maintenance for the health, it is recommended to preferably take about 98 g, every other day and for 30 days. In case of diarrhea of the "tourista" type, it is recommended to preferably take about 98 g twice a day for 3 days followed by about 98 g per day for 7 to 15 days. For the case of constipation, it is recommended to preferably take about 49 g per day for 4 days. The composition of the invention can also be given to children above 12 month at the preferred rate of about 24.5 g per day and for younger infants as a supplement to the feeding bottle at the preferred rate of about one tea spoon per day.

The present invention also includes useful pharmaceutical kits, for example, for the prevention of AAD. The kits comprise one or many containers containing a composition according to the present invention. Such kits may additionally include, if desired, one or many conventional pharmaceutical components like, for example, containers containing one or many pharmaceutically acceptable vehicles, or any other additional containers, which will be evident to a person skilled in the art. A kit according to the present invention can advantageously include instructions in the form of a pamphlet or of any other printed support, indicating the quantities of the compositions to be administered, the instructions for the administration, and/or the instructions to mix the components.

The following example serves to illustrate the extent of the use of the present invention and not to limit its scope. Modifications and variations may be made without forgetting the intent and the extent of the invention. Even though other methods or equivalent products equivalent to those that are found herein to test or to realize the present invention may be used, the material and the preferred methods are described.

Example 1

Study Comparing the Efficacy of a Preparation of *Lactobacillus* (BIO-K+) to that of a Placebo in the Prevention of Antibiotic Associated Diarrhea The study described in this example evaluates the utilisation of a preparation of *Lactobacillus* in a lactic ferment in primary prophylaxis of AAD. Consequently, a double blind, randomized, placebo controlled clinical study was realized. Two groups are compared in this study: the experimental group receiving the preparation of *Lactobacillus* and the control group receiving the placebo preparation: whey devoid of any bacterial strain.

Population Studied

The hospitalized adult patients at the Maisonneuve-Rosemont hospital in Montreal, QC, Canada, receiving an antibiotic treatment orally or parenterally for an estimated period of a minimum of 3 days, other than an aminoside or a vancomycine in monotherapy, were eligible for the study. The exclusion criteria included: refusal to participate, impossibility to obtain consent, incapacity to speak French, active diarrhea, a *C. difficile* infection in the 3 months preceding recruitment, confirmed lactose intolerance, uncontrolled inflammatory intestinal disease, and a regular uptake of probiotic. Moreover, patients receiving chemotherapy, radiotherapy, parenteral feeding or enteral feeding via a nasogastric probe, nil per os patients, ostomy bearing patients, patients with a damaged or artificial cardiac valve, and patients with a transplant were excluded from the study.

A written consent was obtained for each participant and the approval of the treating physician was necessary. The research protocol as well as the consent form were submitted to the ethics committee of the hospital and were accepted on Sep. 12, 2003.

Objectives of the Study

The main objective consisted in evaluating the incidence of AAD in each of the two groups, whether it was brought about during hospitalisation or after the patient had been discharged. AAD was defined by the presence of at least 3 liquid stools in a period of 24 hours. In order to ensure that the antibiotic therapy was the cause, all other etiology such as the use of an enema or laxative was excluded. A follow up was planned in order to evaluate the incidence of AAD 21 days after the end of the antibiotic therapy for all the patients, unless an AAD had occurred before this time.

The secondary objectives aimed to evaluate the severity of AAD, the duration of the hospitalization, and the harmlessness of the preparation of the *Lactobacillus*. For the evaluation of the severity of the AAD, the following parameters were evaluated: the presence of *C. difficile* toxin B in the stools, the presence of blood in the stools (via a positive Gaïac test), the presence of fever, the duration of the diarrhea, the average number of liquid stools per day during a diarrheic episode (grouped in three categories: 3 to 4, 5 to 9 or more than 9 liquid stools per day) and the recourse to an antibiotic treatment against AAD.

In order to evaluate the influence of potentially confounding variables, age, clinical indications of treatment, severity of the patients condition, classes of antibiotics used, the length of the antibiotic therapy, the number of antibiotics received, the utilisation of antibiotics in the month preceding the recruitment or during the period of post-prophylactic follow up, the *C. difficile* antecedents, the hospitalization in a care unit contaminated with *C. difficile*, the use of a proton pump inhibitor, the use of laxatives, the use of narcotics, the intake of an oral supplement of magnesium as well as the consumption of yogurt were documented. It is to be noted that patients were advised not to consume yogurt throughout the duration of the study. The severity of the patient's condition was determined by the incidence of clinical gravity obtained with the help of the "All Patient Refined Diagnosis Related Groups" (APR-DRG v12.0) classification system used by the medical archive service of the HMR.

Data Collection and Course of the Study

The potential subjects were identified daily from a list of patients receiving antibiotic therapy. Once the actual and previous files were revised, the patients were interviewed in order to verify if they were eligible and to obtain their consent.

The randomization was made by the research pharmacy of the hospital, according to a pre-established block sequence. Initially, the randomization was made in the 24 hours following the beginning of the antibiotic therapy. After an amendment to the protocol, the patients could be randomized in the 48 hours following the beginning of their antibiotic therapy.

Following the randomization, the patients received either the preparation of *Lactobacillus acidophilus* (1-1492) and *casei*, either the placebo, according to the attributed group. The dosage used was about 49 grams of the preparation (½ cup) once a day for 2 days and about 98 grams (1 cup) once a day for the following days. The total duration of the prophylaxis corresponded to the duration of the antibiotic therapy. The antibiotic therapy consisted in all antibiotic received in a consecutive fashion. The preparations were distributed by the research pharmacy daily during hospitalisation and administered by the nurse. If the patient was discharged from the hospital before the end of the antibiotic therapy, the quantity of cups necessary for the completion of the prophylaxis were given to him.

During antibiotic therapy, the data relative to the intake of antibiotics and to the outbreak of AAD were collected from the medical files every three days. Afterwards, the data was collected at the end of the antibiotic treatment and on day 7, 14 and 21 post-antibiotic therapy. Moreover, in order to evaluate the emergence of unwanted effects, the patients were interviewed five days following the randomization (or at the time of the discharge of the patient if it occurred earlier) in addition to the last day of antibiotic therapy. These modalities of follow up only apply to the period of hospitalization. If the patient was discharged before the end of the follow up, the data were collected by phone interviews conducted at the end of the antibiotic therapy and on day 7, 14 and 21 post-antibiotic therapy. A memory-aid was given to the patient in order for him/her to take down the different information on which he would be questioned.

At any moment, if an AAD occurred, prophylaxis was stopped, and the follow up was limited to the evaluation of the severity of the AAD. If the patient presented an AAD after having left the hospital, he/she had to contact one of the investigators and, if judged appropriate, he/she was invited to the infectious disease clinic of the HMR for a medical evaluation and a stool analysis.

Statistical Analysis

The study was conceived as a function of a sample size of 120 patients per group in order to be able to detect a 50% decrease in the incidence of AAD (i.e. 30% to 15%) between the two groups of treatment for a statistical power of 80% and a confidence level of 95%. This calculation was based on a bilateral hypothesis test for the difference between two proportions.

The characteristics of the patients as well as the efficiency measurements of severity and harmlessness were evaluated in proportions, averages and standard deviation or in median and interquartile intervals. The comparisons of discrete variables between the groups studied were done by a Khi-squared test or an exact Fisher test. Concerning the continuous variables, a Student t-test allowed verification of the statistical significance of the differences observed between the experimental group and the control. All the analyses were bilateral and the α-type error used was 0.05.

For each of the analyses, an approach with the intent to treat was used in order to evaluate the real efficiency of the *Lactobacillus* preparations. To do this, the randomized group of patients was randomized and having received at least one dose of the preparation studied was considered for analysis. For the primary objective, a second analysis according to the per protocol approach was conducted in order to include only the patients who had received a minimum of three doses of the preparation under study, having taken at least 75% of the planned doses and having completed the planned follow-up.

Results

The files of 1422 patients starting an antibiotic therapy were consulted in order to verify their eligibility. Of these, 89 patients were randomized. The reasons for excluding the other patients are described in FIG. 1. Of the 89 randomized patients, five patients were not counted because they had not received a dose or because of an exclusion criterion occurring after the randomization. For the 84 participants analysed, the average duration of the follow up was of 20±12 days and no significant difference between the two groups was noted (p=0.53). Of this number, 58 patients (69.0%) completed the study as planned by the protocol. It is to be noted that three patients of the *Lactobacillus* group passed away during the course of the study. None of these patients had presented AAD and the deaths did not seem to be directly linked to the use of the preparation studied. A diagram of the distribution of the patients is presented in FIG. 1.

Twenty-seven patients refused to participate in the study. Their demographic characteristics as well as the antibiotic therapy are comparable to that of patients having accepted to participate in the study. More women than men refused (66.7% vs. 33.3%), but this distribution is not significantly different from that of patients having accepted to participate (p=0.17).

The basic characteristics of the patients are similar in the two groups as described in table I. Only the use of β-lactamines is not uniformly distributed between the two groups (p=0.02). Therefore, following a logistical regression analysis, this characteristic was not found to be a confounding variable as to the outbreak of the AAD (p=0.08). The population studied is on average 70 years of age and was treated mainly for respiratory tract infections.

The results relative to the incidence of AAD, its severity and the duration of the hospitalisation are presented in table II.

Concerning the main objective of the study, 27% (23/84) of patients developed AAD, i.e. 37.2% (16/34) in the placebo group compared to 17.1% (7/41) in the group receiving the preparation of *Lactobacillus*. This difference is statistically significant (p=0.04). It remains significant when the analysis is limited to patients having completed the study as planned by the protocol (53.3% (16/30) and 25.0% (7/28), respectively; p=0.03). During the hospitalisation, 18.6% (8/43) of the patients of the group developed AAD, as compared to 7.3% (3/41) of patients receiving the *Lactobacillus* preparation. This difference is not statistically significant (p=0.13). From the patients having been discharged from the hospital during the study, more patients developed an AAD in the placebo group as compared to the *Lactobacillus* group, i.e. 34.8% (8/23) and 13.8% (4/29). In this case also, the difference is not significant (p=0.07).

As to the severity of listed AAD, the limited number of analysed patients limits the possible conclusions. In addition, certain measures of severity were not conducted for all the patients. In 65.2% of AAD cases, a stool analysis was done in order to detect the presence of *C. difficile*. Among all the patients having developed an AAD, a positive result was obtained for 43.8% (7/16) of the patients in the placebo group and 14.3 (1/7) of patients receiving the *Lactobacillus* preparation. This difference is however not statistically significant (p=0.051). On the total number of patients analysed, 16.3% (7/43) of the placebo group developed an infection to *C. difficile*, as compared to 2.4% (1/41) in the *Lactobacillus* group. This difference is statistically significant (p<0.05). The detection of blood in the stools by a positive Gaïac test was conducted in 8.7% only of the patients having developed AAD. The body temperature was measured in 65.2% of the patients having developed AAD. For these two variables, no significant difference was noted between the two groups. The average duration of the episode of AAD did not differ between the two groups (p=0.85), not more than the number of stools per day (p=0.13). It is interesting to note that the majority of AAD was developed after the end of the antibiotic therapy, i.e. 75% (12/16) in the placebo group and 71.4% (5/7) in the *Lactobacillus* group (p>0.99). The average delay between the end of the antibiotic treatment and the occurrence of AAD did not differ between the two groups (8.5 days (±6.3) and 4.2 days (±3.8) respectively (p=0.18)).

Among the patients having developed AAD, an antibiotic treatment (per os vancomycine or i.v. or per os metronidazole), given in an empirical fashion, or targeted for a confirmed *C. difficile* infection was used for 81.3% (13/16) and 42.9% (3/7) of the placebo and *Lactobacillus* groups of patients, respectively (p=0.14).

The median duration of hospitalisation of the patients having received the preparation of *Lactobacillus* is shorter than that of the patients having received the placebo. It was of 8 days (6-14.5) for the group receiving the preparation under study and of 10 days (9-8) for the group receiving the placebo. This difference was statistically significant (p=0.048).

Figure 2:
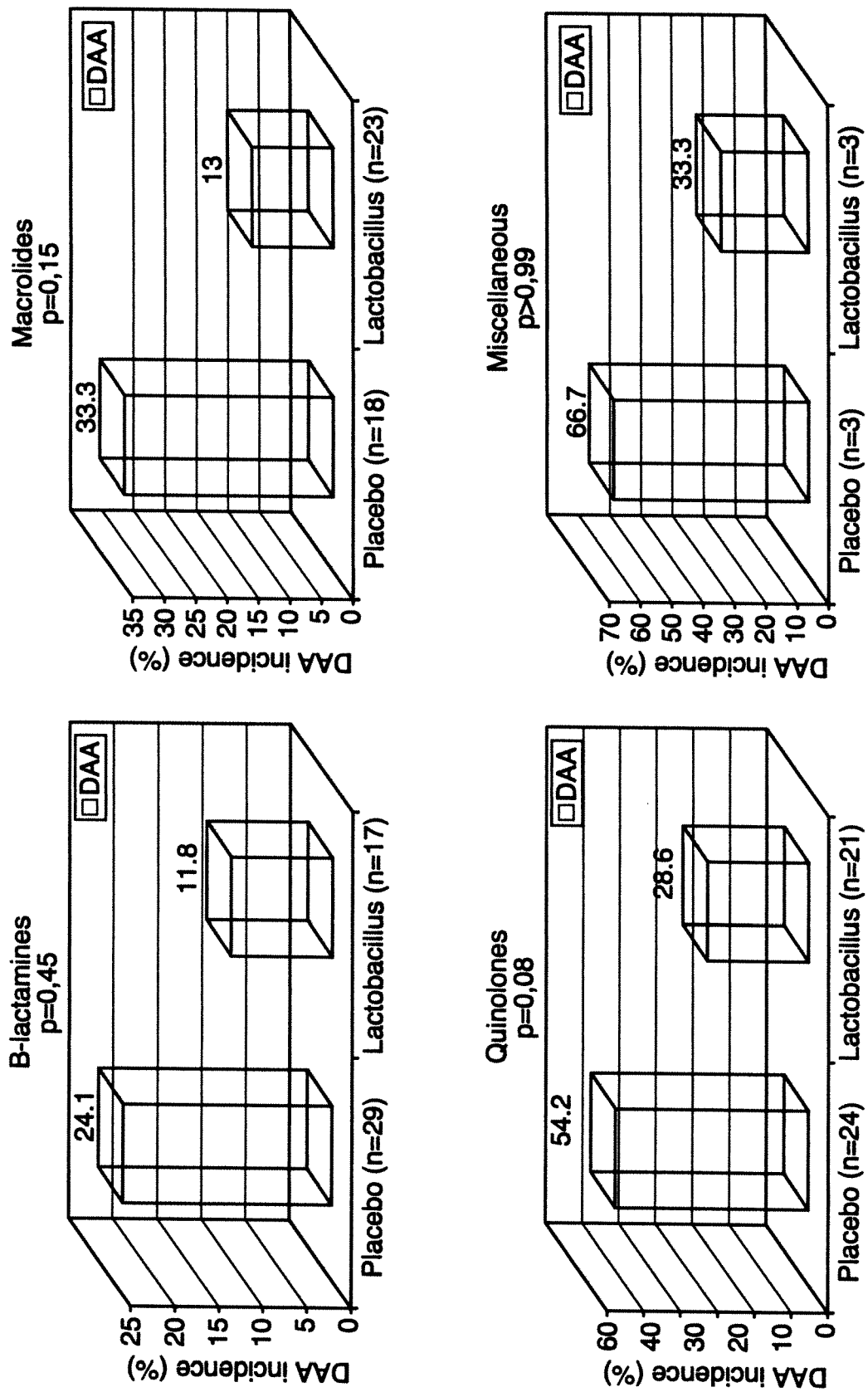
FIG. 2 shows graphics illustrating the incidence of AAD according to the class of antibiotic received in Example 1.
Figure 3:
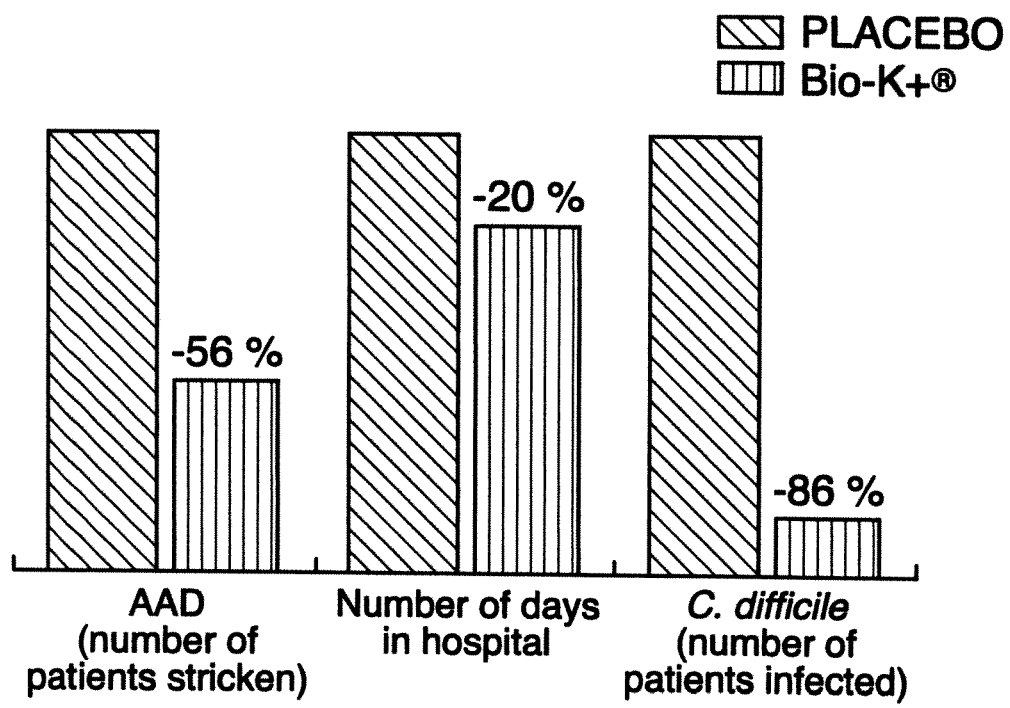
FIG. 3 summarizes the results of the study described in Example 1

The efficacy of the preparation of *Lactobacillus* relative to that of the placebo was also compared according to the classes of antibiotics used (β-lactamines, macrolides, quinolones and diverse antibiotics not listed in other classes). These differences are not statistically significant for each of the classes of antibiotics. The results obtained are illustrated in FIGS. 2 and 3.

Concerning the innocuity of the product under study, the incidence of each of the unwanted manifestations is reported in table ill for the two groups. At least one unwanted effect was reported by 48.8% of the patients, and this in each of the two groups. Concerning the incidence of patients having withdrawn after the manifestation of an unwanted effect, it does not differ from one group to another (20.1% (9/43) in the placebo group and 9.8 (4/41) in the *Lactobacillus* group; p=0.15).

Discussion

Although many studies have evaluated the efficiency of probiotics in the primary prevention of AAD, few conclusive clinical data are available and the results obtained to this day are mixed (Siitonen et al., 1990; Cremonini, et al., 2002; Thomas et al., 2001; Tankanow et al., 1990; Armuzzi, et al., 2001; McFarland et al., 1995; Surawicz et al., 1989; Arvola et al., 1999; Adam et al., 1977; Gotz et al., 1979; Lewis et al., 1998). In certain studies, a decrease in the severity of AAD or a delay in their appearance have been observed without necessarily being related to a significant decrease of their incidence (Siitonen et al., 1990; McFarland et al., 1995; Arvola et al., 1999; Vanderhoof et al., 1999). Moreover, important gaps were present relative to the duration of the follow up, of the definitions of AAD used, of the characteristics of the recruited patients or of the antibiotics included in the studies (Lewis et al., 1998; Surawicz et al., 1989; Stoddart et al., 2002). The duration of the prophylaxis (5-21 days) and the doses used were also very variable (D'Souza et al., 2002).

In addition, the majority of published studies use lyophilized probiotics in the form of a capsule and different strains are evaluated. However, it is important to mention that all probiotics do not act in the same manner and that they may have different clinical efficiencies. The results obtained in the different studies should therefore not be considered valid for strains other than those evaluated in these trials (Cremonin et al., 2002; D'Souza et al., 2002). To this day, no published study had evaluated the efficiency of the combination used in this study, i.e. *Lactobacillus acidophilus*, *Lactobacillus acidophilus* 1-1492 and *Lactobacillus casei*.

In the present Example, different parameters were studied in order to remedy certain gaps observed in the above listed studies. Hence, an objective and reproducible definition of AAD was used, i.e. the presence of three liquid stools or more per 24 hours. This definition leaves little room to interpretation by the patient, the care personnel and the investigators. Furthermore, the duration of the prophylaxis, established according to the duration of the antibiotic therapy is a strategy offering an equivalent protection for all patients, contrary to a fixed duration.

In the present Example, the utilisation of a lactic ferment enriched with *Lactobacillus acidophilus*, *Lactobacillus acidophilus* 1-1492 and *casei* of about 98 grams (1 cup) once a day (about 49 grams on the first two days) proved efficient in the primary prevention of AAD. Although the size of the sample initially determined foresaw the randomization of 240 patients, a statistically significant difference could be observed between the two groups with a sample limited to 84 patients. This observation may be explained, among other things, by the marked incidence of AAD during the study (37.2% in the placebo group), proven higher than the predicted 30% in the calculation of the sample size. This incidence is among the highest ever reported in the literature, which coincides, among other things, with the increase of the number of AAD cases of *C. difficile* noted throughout the course of these past few years.

It must be mentioned that 52.1% (12/23) of AAD occurred at home. The follow up subsequent to the patient's discharge was therefore necessary to ensure a more complete evaluation of the real risk of AAD. A follow up at home is equally pertinent in the actual context of the ambulatory turn in health care systems where the duration of the hospitalisation is shortened. It is useful to alert the patients since the complications that may occur at home eventually have repercussions on the hospital milieu.

A post-antibiotic follow up was particularly important since almost 75% of the observed AAD occurred after the antibiotic therapy, and this in the two groups. Although AAD may occur up until 6 weeks after the end of the antibiotic therapy, the post-antibiotic follow up was limited to 3 weeks since the later the diarrhea occurs the more it could be associated to another etiology (McFarland et al., 1995;

Arvola et al., 1999). It is to be noted that the scope of the data for the delay of AAD apparition after antibiotic therapy was large in the two groups: 1 to 20 days in the placebo group and 2 to 11 days in the *Lactobacillus* group. As such, it is possible that certain cases of AAD were not detected if they occurred more than 21 days after the end of the antibiotic therapy.

The average 20 days duration of the follow up, including the duration of the antibiotic therapy, may seem surprising since it is deemed shorter than the planned post-antibiotic therapy follow up of 21 days. This may be explained by the fact that for 21% of the patients, the planned follow up was not completed (withdrawal, loss of the follow up, death or non respect of the protocol). Also, the follow up was shorter when there was a hasty presentation of AAD.

The development of a *C. difficile* AAD is a parameter of severity important to consider given the clinical and financial implications, which are associated to it. Moreover, it is interesting to note that the composition under study significantly decreases the incidence of *C. difficile* AAD. In the literature, it is reported that the infections due to *C. difficile* represent 10 to 20% of all the cases of AAD (D'Souza et al., 2002; Gaynes et al., 2004). In the actual context of the outbreak of *C. difficile* infections in the hospital milieu, the results of the study suggest rather a proportion of 50%, such as that observed in the placebo group. Although this value may be overestimated given the low number of patients in the study, this proportion is probably closer to the actual reality.

The duration of the hospitalization was shorter in the group of *Lactobacillus*. This observation is explained by the efficiency of the preparation of *Lactobacillus* to decrease the incidence of AAD. However, the possible impact of the gravity of the basic medical condition of the patients must be considered. Indeed, although it was not significantly different between the two groups, it is noted that the group of *Lactobacillus* group includes less cases of extreme gravity and more cases of low gravity than the placebo group.

Many patients presented at least one unwanted effect, i.e. 48.8% in each of the two groups, the majority of which affected the gastro intestinal system. This incidence is high, but no serious unwanted effect was declared. Nonetheless, a non-negligible number of patients withdrew after the occurrence of unwanted effects. These data suggest a potential observance problem, during the course of the study as well as during the ulterior use of the preparation in common practice. Also, it is surprising to observe as high an incidence in unwanted manifestations in the placebo group. However, that the placebo was whey having a particular taste and that the utilisation may be associated to digestion troubles must be considered.

In conclusion, a lactic ferment enriched with a combination of *Lactobacillus acidophilus, Lactobacillus acidophilus* CNCM 1-1492 and *casei* by 98 grams per day allowed the reduction of AAD incidence in 84 hospitalized adult patients receiving a curative antibiotic therapy. The preparation of *Lactobacillus* also allowed a significant decrease of the duration of the hospitalisation. Too few patients were randomized in order to detect an effect of the preparation on the severity of the AAD. The incidence of *C. difficile* AAD was lower in the treated group.

Example 2

Efficacy of Probiotics in Solving an Outbreak of Severe *Clostridium difficile* Colitis at the Pierre-le Gardeur Hospital Centre Introduction:

*Clostridium difficile* colitis is a frequent nosocomial infection in the Pierre-le Gardeur hospital centre (Montreal region, Quebec, Canada). Indeed, during the 2002-2003 fiscal year, the incidence was 9.5 cases/1000 admissions. However, these infections, even the recurrent ones, did not present any severity and responded to a standard metronidazole or oral vancomycin treatment.

Between August and October 2003, there was nearly a 50% increase in the incidence of nosocomial cases with a severity and a mortality rarely encountered with this type of pathology. Furthermore, the response to the usual treatment was at times slow, and even without effect.

In November 2003, a series of measures to counter the situation were taken. The infected patients were isolated as a cohort with dedicated personnel. In addition, a more rigorous maintenance of the hospital was conducted, with disinfection of the bathrooms, the floors and the walls mainly in the rooms where the patients with diarrhea were residing. Also, the medical equipment was disinfected between uses with each and every patient (armbands, hand mixing bowls, etc.). Antibiotics were continued ($2^{nd}$ and $3^{rd}$ generation cephalosporins) and moxifloxacin was removed. Indeed, this antibiotic was involved in 35% of the cases between August and October 2003 (15% when used alone). Subsequently, up to 5.6% of patients taking moxifloxacin developed *C. difficile* colitis (2.2% when used alone). In comparison, 4.6% of the patients treated with $2^{nd}$ and $3^{rd}$ generation cephalosporins suffered from colitis (1.2% if used alone) and only 0.9% of those treated with clindamycin were affected (0.4% when used without association). This association between the quinolones and pseudomembranous colitis has been described in recent publications (Gaynes et al., 2004 and McCusker at al. 2003).

Regardless of these measures, the incidence progressed. Consequently, on Feb. 1, 2004, probiotics were given to all of patients undergoing antibiotic therapy. Decreasing the incidence of severe cases of *C. difficile* colitis was the main objective.

Methodology:

The Pierre-Le Gardeur Hospital Center is a non-university hospital of 250 beds. However, since Apr. 16, 2004 the hospital center has moved to a new building of 284 beds. The study was conducted between Feb. 1, 2004 and Aug. 31, 2004. Because of the numerous shutdowns in services during the move, the incidence of *C. difficile* during the month of April was not considered in the study.

All the patients, those hospitalized and those undergoing antibiotic therapy under observation in the emergency ward, received a probiotic over the period of one month. The probiotic used was the Bio-K+ (International Inc.). This product contains *Lactobacillus acidophilus* (1-1492), which is a strain of human origin, characterized at the Pasteur Institute. The product exists as two forms: as a fresh product of about 98 g of the composition containing about 50 billions bacteria and as a capsule containing about 30 billions bacteria he dosage used was that of a about 98 g jar per day (given during the months of February and March 2004) or of 2 capsules per day (given at the beginning of May 2004 onwards). The probiotic was distributed by the hospital Pharmacy. A permanent prescription was made in order to ensure the rapid start of the probiotic treatment when antibiotic therapy began.

The incidence was calculated every month by reporting the number of new nosocomial cases per 1000 admissions. The nosocomial cases were determined according to the criteria of the CDC in Atlanta (Garner et al. 1988). However, the patients who had received antibiotic therapy and who were kept under observation in the emergency ward without being hospitalized for 3 days and more were also included in the study. The relapsing cases were only tabulated once. Furthermore, the nosocomial cases were subdivided according to their severity. The severity was defined by the presence of at least one of the following: requirement for intensive care, sceptic shock, toxic megacolon, necessity of a colectomy, slow or absent response to treatment (>48 hours) and mortality.

The detection of the *C. difficile* A/B toxin was done with an ELISA test from the company R-Biopharm (Ridascreen™). The tests were conducted five times a day on a stool sample without preservatives.

The observance of the treatment by the patients undergoing probiotic therapy (fresh product only) was analyzed during three days during the month of March 2004. The patients who had not observed the treatment were asked why they did not observe it. This analysis was not conducted for the patients taking the capsules since no problem with respect of that product was observed. The observance of the treatment by the patients in the community was not verified, but a prescription was given to the patient after discharge.

Figure 4:
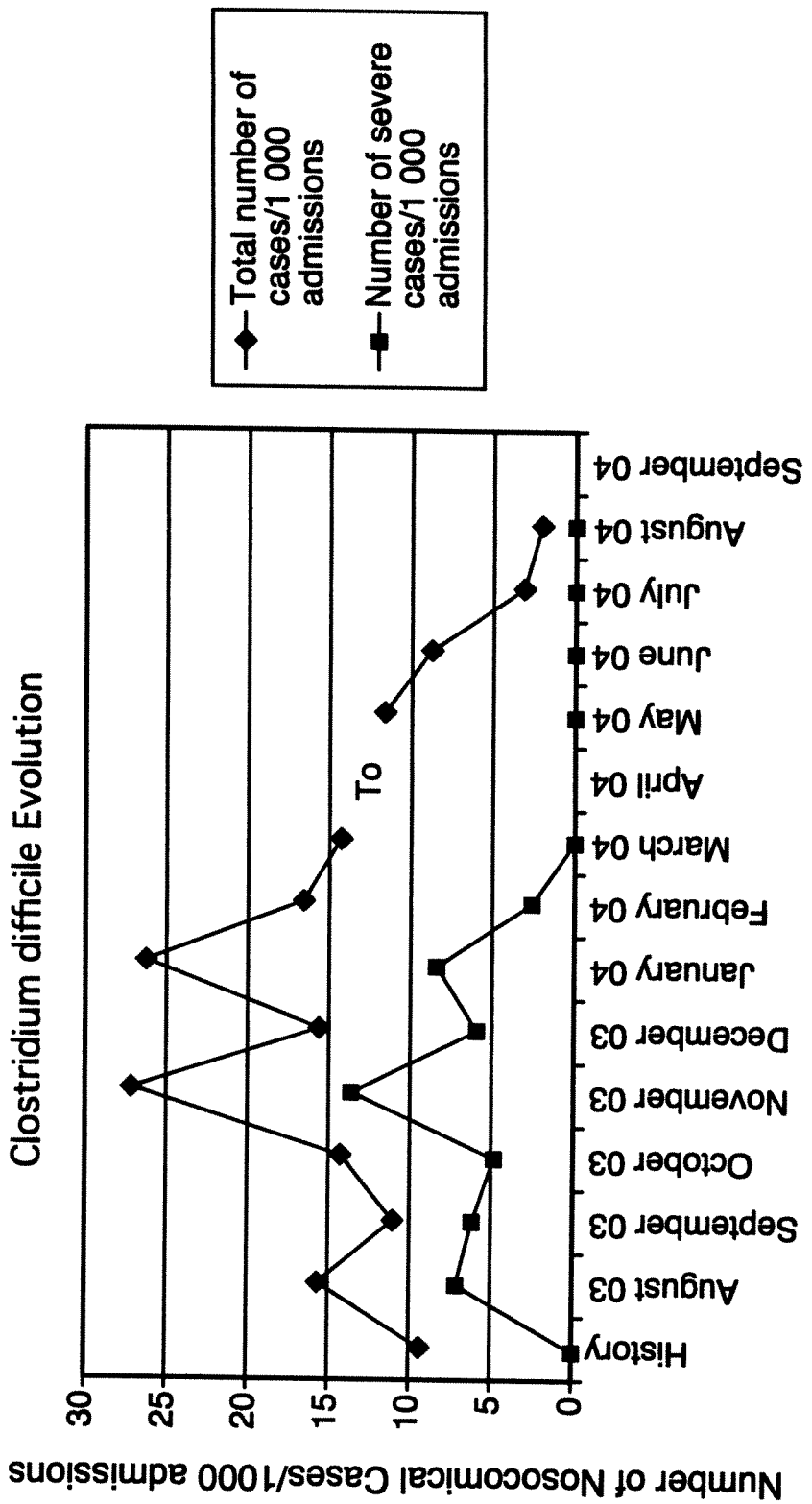
FIG. 4 shows the evolution in time of *C. difficile* infection in the study described in Example 2.

Results:

A total number of 2544 patients received the probiotic between February 1$^{st}$ and Aug. 31, 2004. The results are summarized in FIG. 4.

The average incidence of severe cases during the outbreak was 7.7 cases/1000 admissions (between August 2003 and January 2004). After the first month of the study, the incidence fell to 2.6 cases/1000 admissions (a 66% decrease). In addition, since March 2004, there were no longer severe cases. There were 10 cases of direct mortality between August 2003 and January 2004. A patient underwent a total colectomy in November 2003. The last case of mortality dated back to January 2004. The total incidence had also decreased. Indeed, the present incidence (2.1 cases/1000 admissions) is 78% less than what it was before the outbreak (9.5 cases/1000 admissions). No new cases in isolation for *C. difficile* were declared since Aug. 11, 2004.

Concerning compliance, 201 observations were made during 3 days. An observance rate of 66% for the fresh product was recorded. 23% of patients who were under observation refused to take the probiotic and 11% took it partially. The main reason for the lack of observance for the treatment was the taste of the product (even for the fruit flavoured product).

The estimated annual cost of the capsules is of CAN $10 000.00, whereas the cost of the fresh product is of around CAN $25 000.00.

Discussion:

The use of probiotics (*Lactobacillus*, *Saccharomyces boulardii*) was proven to be efficient in the primary prevention of antibiotic associated diarrhea. A recent meta-analysis mentions it (D'Souza et al. 2002). The principle is to reconstitute the intestinal flora destroyed in part by the antibiotic therapy.

Massive use of probiotics in Legardeur Centre has yielded very rapid results. Indeed, regardless of an improved environmental hygiene, it was impossible to control the outbreak. This may be explained by the fact that the old location of Centre was difficult to maintain. There were few bathrooms and an important number of patients were found in the hallways of the emergency wards and of the different units. The other explanation is that the critical mass of infected patients or those colonized with that particular strain of *C. difficile* had become too important.

The new hospital centre presents a certain advantage at the level of the cleanliness of the environment. Indeed, 70% of the rooms are individual rooms, each furnished with a bathroom. The other rooms are conceived for two patients and are also provided with a bathroom facility. No room may accommodate four patients. Also, there are no more hallways in the emergency ward. Regardless of these improvements, it is important to note that the nosocomial *C. difficile* cases had already started to decrease significantly two months after the move.

Regardless of a retrospective comparison in this study to determine the efficacy of probiotics, the rapid control of this severe outbreak and the reduced cost of this measure are elements that hospitals must seriously consider when faced with this problematic.

TABLE I

Basic characteristics of 89 randomized patients*

| Characteristics | Placebo (N = 45) | *Lactilobacillus* preparation (N = 44) | p value |
|---|---|---|---|
| Average age (years) | 72.9 ± 13.5 | 68.8 ± 14.5 | 0.14 |
| Average number of antibiotic(s) | 2.4 ± 1.2 | 2.0 ± 1.0 | 0.13 |
| Average duration of antibiotherapy (days) | 9.8 ± 4.4 | 8.8 ± 3.7 | 0.29 |
| Average duration under prophylaxis (days) | 7.3 ± 4.3 | 7.6 ± 4.3 | 0.74 |
| Male | 23 (51.0) | 20 (45.5) | 0.59 |
| Clinical indications | | | |
| Respiratory infection | 41 (91.1) | 40 (90.9) | 0.97 |
| Other infections$^§$ | 4 (8.9) | 4 (9.1) | |
| Antibiotic categories | | | |
| β-lactamines$^&$ | 30 (66.7) | 18 (40.9) | 0.02 |
| Macrolides | 25 (55.6) | 27 (61.4) | 0.58 |
| Quinolones | 28 (62.2) | 25 (56.8) | 0.60 |
| Various | 6 (13.3) | 6 (13.6) | 0.97 |
| Clinical gravity index (APR-DRG)$^¥$ | | | |
| 1- Low | 2 (4.7) | 6 (15.8) | 0.14 |
| 2- Moderate | 20 (46.5) | 18 (47.4) | 0.94 |
| 3- High | 14 (32.6) | 13 (34.2) | 0.88 |
| 4- Extreme | 7 (16.3) | 1 (2.6) | 0.06 |
| Hospitalisation on a care unit contaminated with *C. difficile* | 34 (75.6) | 30 (68.2) | 0.44 |
| *C. difficile* antecedent | 4 (8.9) | 2 (4.5) | 0.68 |
| DAA antecedent | 9 (20.0) | 8 (18.2) | 0.83 |
| PPI usage | 18 (40.0) | 15 (34.1) | 0.56 |
| Magnesium oral supplement usage | 2 (4.4) | 2 (4.5) | >0.99 |
| Laxative(s) usage | | | |
| None | 30 (66.7) | 34 (77.3) | |
| Occasionally | 5 (11.1) | 5 (11.4) | 0.39 |
| Regularly | 10 (22.2) | 5 (11.4) | |
| Narcotic(s) usage | | | |
| None | 31 (68.9) | 32 (72.7) | |
| Occasionally | 9 (20.0) | 10 (22.7) | 0.51 |
| Regularly | 5 (11.1) | 2 (4.5) | |
| Yogurt consumption | 9 (20.0) | 5 (11.4) | 0.26 |
| Antibiotherapy in the month preceding randomisation | 9 (20.0) | 9 (20.5) | >0.99 |

*data is presented as number of patients (percentage) or as average ± Standard deviation;
DAA: diarrhoea associated with antibiotics;
PPI: proton pump inhibitor.
$^§$include: urinary infections, skin and limp tissues infections;
$^&$include penicillins and cephalosporins;
$^¥$8 missing results (placebo group: n = 2, *lactobacillus* group: n = 6)

TABLE II

Incidence and severity of DAA and hospitalization duration*

| Incidence of DAA | Placebo (N = 43) | Lactilobacillus preparation (N = 41) | p value |
|---|---|---|---|
| DAA | 16 (37.2) | 7 (17.1) | 0.04 |
| Occurred during hospitalisation | 8/43 (18.6) | 3/41 (7.3) | 0.13 |
| Ocurred at home | 8/23 (34.8) | 4/29 (13.8) | 0.07 |
| Severity of DAA | | | |
| Presence of *C. difficile* toxin | 7/43 (16.3) | 1/41 (2.3) | <0.05 |
| Blood in stools | | | |
| Positive Gaïac test | 2/16 (12.5) | 0/7 (0) | >0.99 |
| Fever | | | |
| Average length of DAA (days) | 2/16 (12.5) | 1/7 (14.3) | >0.83 |
| Average number of liquid stools$^¥$ | 4.6 ± 3.6 | 5 ± 4.4 | 0.85 |
| 3 to 4 | 7/16 (43.8) | 3/7 (42.9) | |
| 5 to 9 | 7/16 (43.8) | 2/7 (28.6) | 0.13 |
| >9 | 2/16 (12.5) | 0/7 (0) | |
| DAA necessitating treatment | 13/16 (81.3) | 3/7 (42.9) | 0.14 |
| Hospitalisation length | | | |
| Median duration | 10 (8-19) | 8 (6-14.5) | 0.048 |

*data is presented as number of patients (percentage), as average ± Standard deviation or as median (interquartile interval)
$^¥$2 missing results in the *lactobacillus* group

TABLE III

Undesirable effects reported during the study*

| | Placebo (N = 43) | Lactilobacillus preparation (N = 41) |
|---|---|---|
| Presence of at least one undesirable effect - n.b. (%) | 21 (48.8) | 20 (48.8) |
| Softening of the stools | 9 (20.1) | 8 (19.5) |
| Bad taste | 7 (16.3) | 6 (14.6) |
| Abdominal cramps | 5 (11.6) | 4 (9.8) |
| Bloating | 3 (7.0) | 3 (7.3) |
| Nauseas | 4 (9.3) | 0 |
| Gastro-oesophagal reflux | 2 (4.7) | 2 (4.9) |
| Modified stool color | 2 (4.7) | 1 (2.4) |
| Constipation | 1 (2.3) | 2 (4.9) |
| Flatulence | 1 (2.3) | 2 (4.9) |
| Regurgitation | 1 (2.3) | 0 |
| Putrid stool odor | 1 (2.3) | 0 |
| Rash | 1 (2.3) | 0 |
| Pruritus | 0 | 1 (2.4) |
| Undesired effect leading to retrieval of study - nb. (%) | 9 (20.1) | 4 (9.8) |

*No statistical difference has been detected between the two groups for each variable

*Lactobacillus acidophilus* (accession number I-1492) herein described was deposited on Nov. 15, 1994 at the Collection National de Cultures de Microorganismes (CNCM; an International Depository Authority, whose full post office address is Institut Pasteur, 28 Rue du Docteur Roux, F-75724, Paris CEDEX 15, France) according to the provisions of the Budapest Treaty.

REFERENCES

1. Hőgenauer C, Hammer H F, Krejs G J, et al. Mechanisms and management of antibiotic-associated diarrhea. Clin Infect Dis 1998; 27: 702-10.
2. Miller M A, Hyland M, Ofner-Agostini M, et al. Morbidity, mortality, and healthcare burden of nosocomial *Clostridium difficile*-associated diarrhea in Canadian hospitals. Infect Control Hosp Epidemiol. 2002 March; 23(3):137-40.
3. Dionne J-Y. Les probiotiques, bien plus qu'un yogourt! L'actualite pharmaceutique 2003; 11(3): 32.
4. Siitonen S, Vapaatalo H, Salminen S, et al. A. Effect of *Lactobacillus* GG yoghurt in the prevention of antibiotic-associated diarrhoea. Ann Med 1990; 22: 57-9.
5. Cremonini F. Di Caro S, Nista E C, et al. Meta-analysis: the effect of probiotic administration on antibiotic-associated diarrhea. Aliment Pharmacol Ther 2002; 16:1461-67.
6. Lu L, Walker W A. Phatologic and physiologic interactions of bacteria with the gastrointestinal epithelium. Am J Clin Nutr 2001; 73: 1124S-30S.
7. Lewis S J, Freedman A R. Review article: the use of biotherapeutic agents in the prevention and treatment of gastrointestinal disease. Aliment Pharmacol Ther. 1998; 12:807-22.
8. D'Souza A L, Rajkumar C, Cooke J, et al. Probiotics in prevention of antibiotic associated diarrhoea: meta-analysis. BMJ 2002; 324: 1361.
9. Isolauri E. Probiotics in human disease. Am J Clin Nutr 2001; 73: 1142S-6S.
10. Alvarez-Olmos M I, Oberhelman R A. Probiotic agents and infectious diseases: A modern perspective on a traditional therapy. Clin Infect Dis 2001; 32: 1567-76.
11. Thomas M R, Litin S C, Osmon D R, et al. Lack of effect of *Lactobacillus* GG on antibiotic-associated diarrhea: a randomized, placebo-controlled trial. Mayo Clin Proc 2001 September; 76(9):883-9.
12. Tankanow R M, Ross M B, Ertel I J, et al. Double blind, placebo-controlled study of the efficacy of Lactinex in the prophylaxis of amoxicillin-induced diarrhoea. DICP 1990; 24: 382-4.
13. Armuzzi A, Cremonini F, Bartolozzi F, et al. The effect of oral administration of *Lactobacillus* GG on antibiotic-associated gastrointestinal side-effects during *Helicobacter pylori* eradication therapy. Aliment Pharmacol Ther 2001; 15: 163-169.
14. McFarland L, Surawicz C M, Greenberg R N, et al. Prevention of β-lactam-associated diarrhea by *Saccharomyces boulardii* compared with placebo. Am J Gastroenterol 1995; 90 (3): 439-48
15. Surawicz C M, Elmer G W, Speelman P, et al. Prevention of antibiotic associated diarrhoea by *Saccharomyces boulardii*. Gastroenterology 1989; 96: 981-8.
16. Arvola T, Laiho K, Torkkeli S, et al. Prophylactic *Lactobacillus* GG reduces antibiotic-associated diarrhea in children with respiratory infections: a randomized study. Pediatrics 1999; 104(5):A64 (Abstract).
17. Adam J, Barret A, Barret-Bellet C. Essais cliniques contrôles en double insu de l'Ultra-levure lyophilisee: etude multicentrique par 25 medecins de 388 cas. Gaz Med Fr 1977; 84: 2072-8.
18. Gotz V, Romankiewicz J A, Moss J, et al. Prophylaxis against ampicillin-associated diarrhoea with a *Lactobacillus* preparation. Am J Hosp Pharm 1979; 36: 754-7.
19. Lewis S J, Potts L F, Barry R E. The lack of therapeutic effect of *S boulardii* in the prevention of antibiotic related diarrhoea in elderly patients. J Infect 1998; 36: 171-4.
20. Vanderhoof J A, Whitney D B, Antonson D L, et al. *Lactobacillus* GG in the prevention of antibiotic-associated diarrhoea in children. J Pediatrics 1999; 135: 564-8.
21. Stoddart B, Wilcox M H. *Clostridium difficile*. Curr Opin Infect Dis 2002; 15: 513-18.

22. Gaynes R, Rimland D, et al. Outbreak of *Clostridium difficile* infection in a long-term care facility: Association with gatofloxacin use. Clin. Infect Dis 2004; 38: 640-5.
23. McCusker M E, Harris A D, et al. Fluoroquinolone use and *Clostridium difficile*-associated diarrhea. Emerg. Infect Dis 2003; 9: 730-3.
24. Garner J S, Jarvis W R, et al. CDC definitions for nosocomial infections. Am J Infect Control 1988; 16: 128-40.
25. Bergogne-Berezin E. Treatment and prevention of antibiotic associated diarrhea. Int J Antimicrob Agents 2000; 16: 521-26.
26. McFarland L V. Facteurs de risque de la diarrhee associee aux antibiotiques. Ann Med Interne 1998; 149 (5):261-6.
27. Spencer R C. The role of antimicrobial agents in the aetiology of *Clostridium difficile*-associated disease. J Antimicrob Chem 1998; 41(Suppl C):21-7.
28. Bartlett J G. Antibiotic-associated diarrhea. N Engl J Med 2002; 346(5): 334.
29. McFarland L V, Elmer G W, Surawicz C M. Breaking the cycle: treatment strategies for 163 cases of recurrent *Clostridium difficile* disease. Am J Gastroenterol 2002; 97: 1769-75.
30. McFarland L V, Mulligan M E, Kwok R Y Y et coll. Nosocomial acquisition of *Clostridium difficile* infection. N Engl J Med 1989; 320: 204-10

The invention claimed is:

1. A method of preventing antibiotic associated diarrhea (AAD) comprising orally administering to a human adult receiving an antibiotic therapy a fermented food product consisting of a mixture of Lactobacilli and fermented proteins,
   wherein the mixture of Lactobacilli comprises *Lactobacillus acidophilus* I-1492 strain deposited at the CNCM and a *Lactobacillus casei* strain, and
   wherein said method prevents AAD by reducing at least one of incidence of antibiotic associated diarrhea (AAD), severity of AAD, or duration of AAD.

2. The method of claim 1, wherein the fermented proteins comprise fermented soy proteins.

3. The method of claim 1, wherein the fermented food product is a food supplement.

4. The method of claim 1, wherein the fermented food product is administered as a gel or a capsule.

5. The method of claim 4, wherein the gel or the capsule comprises at least 50 billion colony forming units (CFUs) of a population of living and active micro-organisms of the *Lactobacillus acidophilus* I-1492 strain.

6. The method of claim 4, wherein the gel or the capsule comprises at least 100 billion colony forming units (CFUs) of a population of living and active micro-organisms of the *Lactobacillus acidophilus* I-1492 strain.

7. The method of claim 1, wherein the antibiotic associated diarrhea is caused by a *Clostridium difficile* infection.

8. The method of claim 1, wherein the mixture of Lactobacilli consists essentially of the *Lactobacillus acidophilus* I-1492 strain deposited at the CNCM and a *Lactobacillus casei* strain.

9. The method of claim 1, wherein the mixture of Lactobacilli consists of the *Lactobacillus acidophilus* I-1492 strain deposited at the CNCM and a *Lactobacillus casei* strain.

10. The method of claim 1, wherein said method reduces duration of hospitalization of the patient as compared to duration of another hospitalized patient receiving the same antibiotic therapy but not the fermented food product.

11. The method of claim 1, wherein said method reduces presence of blood in stools of the subject compared to another subject receiving the same antibiotic therapy but not the fermented food product.

12. The method of claim 1, wherein the method prevents AAD by reducing an average number of liquid stools in the subject compared to another subject receiving the same antibiotic therapy but not the fermented food product.

13. The method of claim 1, wherein the composition is administered within 48 hours following beginning of antibiotic therapy or for a total duration of antibiotic therapy.

14. A method of preventing antibiotic associated diarrhea (AAD) comprising orally administering to a human adult receiving an antibiotic therapy a fermented food product consisting of a mixture of Lactobacilli and fermented proteins, wherein the mixture of Lactobacilli comprises *Lactobacillus acidophilus* I-1492 strain deposited at the CNCM and a *Lactobacillus casei* strain, and
   wherein said fermented food product is administered within 48 hours following beginning of antibiotic therapy or for a total duration of antibiotic therapy.

15. The method of claim 14, wherein the fermented proteins comprise fermented soy proteins.

16. The method of claim 14, wherein the fermented food product is a food supplement.

17. The method of claim 14, wherein the fermented food product is administered as a gel or a capsule.

18. The method of claim 17, wherein the gel or the capsule comprises at least 50 billion colony forming units (CFUs) of a population of living and active micro-organisms of the *Lactobacillus acidophilus* I-1492 strain.

19. The method of claim 17, wherein the gel or the capsule comprises at least 100 billion colony forming units (CFUs) of a population of living and active micro-organisms of the *Lactobacillus acidophilus* I-1492 strain.

20. The method of claim 14, wherein the antibiotic associated diarrhea is caused by a *Clostridium difficile* infection.

21. The method of claim 14, wherein the mixture of Lactobacilli consists essentially of the *Lactobacillus acidophilus* I-1492 strain deposited at the CNCM and a *Lactobacillus casei* strain.

22. The method of claim 14, wherein the mixture of Lactobacilli consists of the *Lactobacillus acidophilus* I-1492 strain deposited at the CNCM and a *Lactobacillus casei* strain.

23. A method of preventing antibiotic associated diarrhea (AAD) comprising orally administering to a human adult receiving an antibiotic therapy a fermented food product consisting of a mixture of Lactobacilli and fermented proteins,
   wherein the mixture of Lactobacilli comprises *Lactobacillus acidophilus* I-1492 strain deposited at the CNCM and a *Lactobacillus casei* strain, and
   wherein said fermented food product is administered within 48 hours following beginning of antibiotic therapy or for a total duration of antibiotic therapy.

* * * * *